(12) United States Patent
Stamler (10) Patent No.: US 11,577,042 B2
(45) Date of Patent: Feb. 14, 2023

(54) VAPORIZATION SYSTEM FOR DELIVERY IN A CONTROLLED CONCENTRATION

(71) Applicant: CASE WESTERN RESERVE UNIVERSITY, Cleveland, OH (US)

(72) Inventor: Jonathan S. Stamler, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 451 days.

(21) Appl. No.: 16/619,202

(22) PCT Filed: Jun. 7, 2018

(86) PCT No.: PCT/US2018/036412
§ 371 (c)(1),
(2) Date: Dec. 4, 2019

(87) PCT Pub. No.: WO2018/226928
PCT Pub. Date: Dec. 13, 2018

(65) Prior Publication Data
US 2020/0114110 A1 Apr. 16, 2020

Related U.S. Application Data

(60) Provisional application No. 62/516,973, filed on Jun. 8, 2017.

(51) Int. Cl.
*A61M 16/12* (2006.01)
*A61M 16/10* (2006.01)
(Continued)

(52) U.S. Cl.
CPC ...... *A61M 16/125* (2014.02); *A61M 16/0057* (2013.01); *A61M 16/0066* (2013.01);
(Continued)

(58) Field of Classification Search
CPC .............. A61M 16/00; A61M 16/0057; A61M 16/022; A61M 16/024; A61M 16/08;
(Continued)

(56) References Cited

U.S. PATENT DOCUMENTS 5,607,000 A 3/1997 Cripe et al.
10,300,226 B2 * 5/2019 Cohen ................. A61M 16/109
(Continued)

FOREIGN PATENT DOCUMENTS

CN 101868277 A 10/2010
EP 2 832 393 A1 2/2015
(Continued)

OTHER PUBLICATIONS

Moya, Martin P. et al, "Inhaled Ethyl Nitrite Gas for Persistent Pulmonary Hypertension of the Newborn," The Lancet, vol. 360, Issue 9327, ISSN: 0140-6736, DOI: https://doi.org/10.1016/S0140-6736(02)09385-6, dated Jul. 13, 2002, 8 pages.
(Continued)

*Primary Examiner* — Joseph D. Boecker
(74) *Attorney, Agent, or Firm* — Tarolli, Sundheim, Covell & Tummino LLP (57) ABSTRACT

Devices for delivering a controlled concentration of an agent are provided. The device includes a reservoir for the agent and a flow control portion operably connected to the reservoir. The device also includes a valve for releasing the agent from the flow control portion and a pump for flowing air to mix with the agent released by the valve and for flowing the agent and air mixture out of the device. Methods of delivering a vaporized agent to a subject are also provided. The methods include storing a liquid agent in a reservoir of a device and flowing the agent into a flow control chamber to change the agent to a gas. The methods also include mixing
(Continued)

the agent in gas form with air and flowing the agent and air mixture out of the device to be delivered to a subject.

19 Claims, 7 Drawing Sheets

VAPORIZATION SYSTEM FOR DELIVERY IN A CONTROLLED CONCENTRATION

RELATED APPLICATIONS

This application is the national phase application of PCT/US2018/036412, filed on Jun. 7, 2018, which claims the benefit of and priority to, under 35 U.S.C. § 119(e) of U.S. Provisional Application No. 62/516,973, filed Jun. 8, 2017, the entire contents of both of which are incorporated herein by reference in their entirety.

FEDERALLY SPONSORED RESEARCH OR DEVELOPMENT

This invention was made with government support under federal grant number N66001-10-C-2015 awarded by Defense Advanced Research Projects Agency. The government has certain rights in the invention.

BACKGROUND

Technical Field

This application relates to devices and methods for delivery of a controlled concentration of a substance using a vaporization system, and in particular to devices and methods for ambulatory vaporization systems for delivering a nitrosylating agent.

Background Information

Administration of ethyl nitrite (ENO) gas is currently cumbersome and not amenable to ambulatory care. Typically a large tank of ENO gas is needed for delivery of the ENO gas to a subject and the tank is not readily movable by the subject receiving the ENO gas. In addition, the concentration of the ENO delivered to the subject must be controlled so that the ratio of ENO to hemoglobin is regulated.

What is needed is a system and a method for delivering a substance in a controlled concentration that allows for ambulation of the subject receiving the controlled concentration of the substance. What is needed is a system and a method for delivering ENO at concentrations in the range of about 0.1-100 ppm using a device that allows patient mobility.

BRIEF SUMMARY

Devices and methods for delivering a controlled concentration of an agent are provided. The device includes a reservoir for the agent and a flow control portion operably connected to the reservoir. The device also includes a valve for releasing the agent from the flow control portion and a pump for flowing air to mix with the agent released by the valve and for flowing the agent and air mixture out of the device.

In another aspect, methods of delivering a vaporized agent to a subject are provided. The methods include storing a liquid agent in a reservoir of a device and flowing the agent into a flow control chamber to change the agent to a gas. The methods also include mixing the agent in gas form with air and flowing the agent and air mixture out of the device to be delivered to a subject.

In another aspect, the present disclosure relates to a device for delivering a controlled concentration of an agent, the device comprising: (a) a reservoir for the agent; (b) a flow control portion operably connected to the reservoir; (c) a valve for releasing the agent from the flow control portion; and (d) a pump for flowing air to mix with the agent released by the valve and for flowing the agent and air mixture out of the device.

In one embodiment, the flow control portion comprises a capillary tubing system. In one embodiment, the length of the capillary tubing system is about 1 mm to about 1000 mm.

In another embodiment, the flow control portion of the device comprises a gas expansion chamber.

In yet another embodiment, the device further comprises a manifold operably connected to the flow control portion.

In yet another embodiment, the device further comprises a temperature control unit.

In another embodiment, the device further comprises a controller for controlling the flow of the agent through the device. In one embodiment, the controller controls the pump and/or the temperature.

In another embodiment, the reservoir of the device comprises a replaceable cartridge.

In yet another embodiment, the reservoir of the device comprises stainless steel.

In another embodiment, the device further comprises a portion of a manifold that co-extends along at least a portion of the reservoir.

In another embodiment, the device further comprises a battery.

In another embodiment, the device further comprises an agent, wherein the agent comprises liquid ethyl nitrite.

Another aspect of the present disclosure relates to a method of delivering a vaporized agent to a subject, the method comprising: (a) storing a liquid agent in a reservoir of a device; (b) flowing the agent into a flow control chamber to change the agent to a gas; (c) mixing the agent in gas form with air; and (d) flowing the agent and air mixture out of the device to be delivered to a subject.

In one embodiment, the method further comprises heating the liquid agent.

In another embodiment, the method comprises delivering the agent to the subject at a range of about 0.1-100 ppm.

In yet another embodiment, the agent used in the method comprises liquid ethyl nitrite.

In another embodiment, the method further comprises controlling the amount of the agent delivered to the subject by controlling the temperature of the device.

In yet another embodiment, the method further comprises controlling flow out of the flow control chamber with a valve.

In another embodiment, the device used in the method for delivering the agent to the subject is an ambulatory device.

DETAILED DESCRIPTION

The embodiments disclosed below are not intended to be exhaustive or to limit the scope of the disclosure to the precise form in the following description. Rather, the embodiments are chosen and described as examples so that others skilled in the art may utilize its teachings.

Unless specifically stated, as used herein, the term "about" refers to a range of values±10% of a specified value. For example, the phrase "about 200" includes ±10% of 200, or from 180 to 220. When stated otherwise the term about will refer to a range of values that include ±20%, ±10%, or ±5%, etc.

Figure 1:
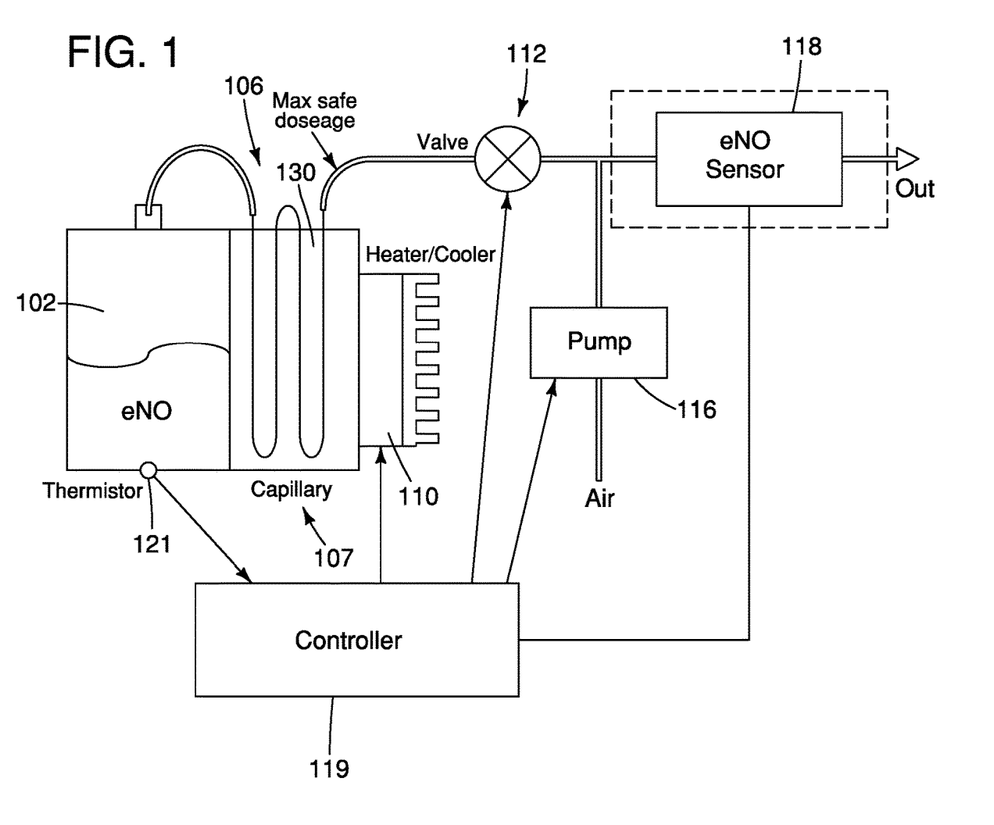
FIG. 1 is a schematic of an embodiment of an ambulatory device.

A schematic view of an embodiment of an ambulatory device 100 for delivery of controlled concentration of a substance is shown in FIG. 1. In some embodiments, the device may be used to deliver a nitrosylating agent to a subject. The nitrosylating agent includes but is not limited to the following: ethyl nitrite, amyl nitrite, butyl nitrite, isobutyl nitrite, tert-butyl nitrite and combinations thereof. In some embodiments, the nitrosylating agent is ethyl nitrite (ENO). The device 100 shown in FIG. 1 is described with reference to ENO as the agent being delivered, however, other agents may also be used. For example, any liquid agent that may be vaporized for delivery to a subject may be delivered using the device 100. The temperature, delivery rate and controller will depend on the agent being delivered.

The device 100 includes a reservoir 102 for storing the agent. The reservoir 102 may be connected to a flow control portion 106 such as a manifold 130 and a capillary tubing system 107 shown in FIG. 1 or a gas expansion chamber 209 (shown in FIG. 8). A temperature controller 110 may be connected to the flow control portion 106. One or more valves 112 control the flow of agent out of the flow control portion 106 to be mixed with fresh air and delivered to the subject. In some embodiments, a pump 116 may be used to pump the air mixed with the agent. A sensor 118 may be included to monitor or control the amount of the agent that is delivered to the subject. A controller 119 may be included in the device 100 to monitor and regulate the temperature of the reservoir 102, the temperature controller 110, the valve 112, the pump 116 and the sensor 118. In some embodiments, a thermistor 121 may be connected to the reservoir 102 and the controller 119.

Figure 2A:
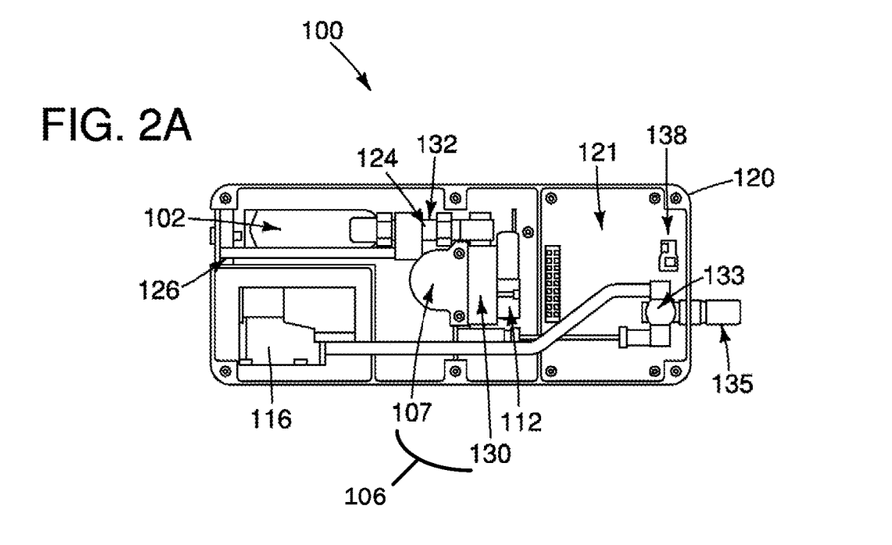
FIG. 2A is a top view of an embodiment of an ambulatory device.
Figure 2B:
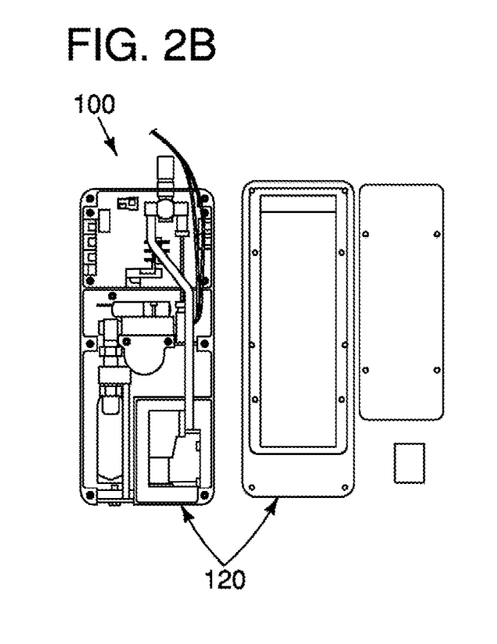
FIG. 2B is a top view of the device shown in FIG. 2A with the casing in an open configuration.
Figure 2C:
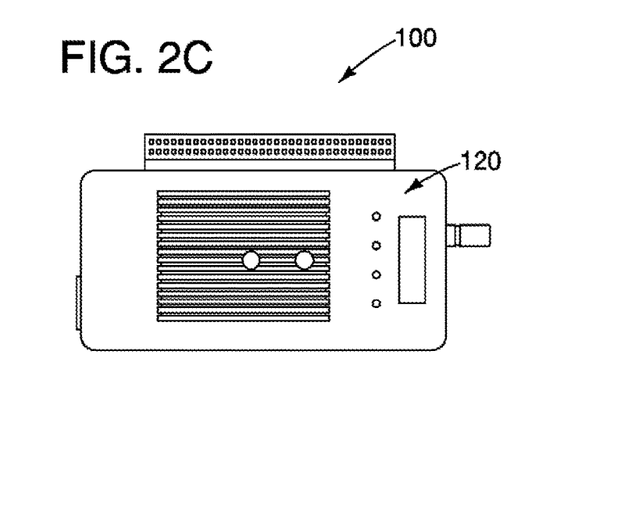
FIG. 2C is a top view of the device shown in FIG. 2A with the casing in a closed configuration.
Figure 5:
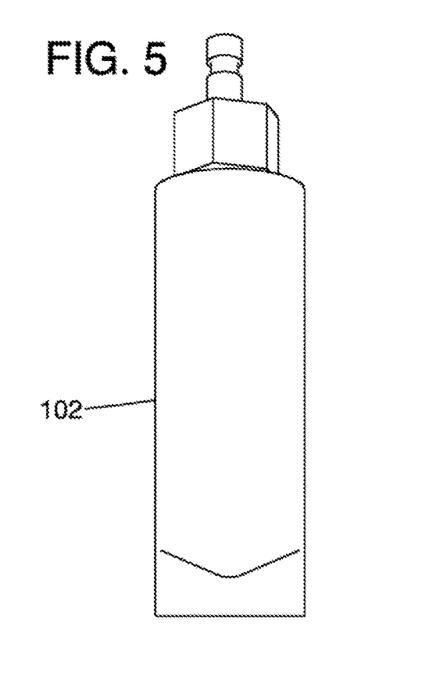
FIG. 5 illustrates a replaceable reservoir of an embodiment of an ambulatory device.

FIG. 2A shows the device 100 assembled together in a casing 120. FIG. 2B shows an open view of the assembled device 100 within the casing 120. Note that insulation that may also be provided is not shown. FIG. 2C shows a top view of the device 100 enclosed in the casing 120. As shown in FIG. 2A, the device 100 may include a reservoir 102 that stores ENO in a mixed phase (liquid and saturated gas) storage cartridge; storage in liquid form allows for a considerable amount of agent to be included in the device 100 relative to the rate of use. The storage cartridge may be made of steel, such as stainless steel or a polymer, such as polycarbonate. In some embodiments, a stainless steel reservoir 102 may be used to improve the thermal conduction between the temperature controller 110 and the reservoir 102. The boiling point of ENO is 63° F. so as a result the vapor pressure generated at temperatures above this point self-propel ENO through the system. In addition, the vapor pressure of ENO is proportional to temperature thus ENO flow may be controlled by the device 100 temperature. As shown in FIG. 2A, the device 100 may include a replaceable cartridge, such as a replaceable ENO cartridge 102. An example of a replaceable cartridge 102 is shown in FIG. 5. The replaceable cartridge 102 may be exchanged through the use of a double shut-off system 124 for quick recharging/re-dosing. The double shutoff system 124 serves to prevent ENO leakage while the mating half-closes to keep contaminates out of the system during a vial exchange. When a replaceable reservoir 102 is included, a release 126 may be include to release the reservoir from the casing 120. The replaceable cartridge 102 may have an internal volume of about 20 ml and be designed to hold about 10 ml of liquid ENO. The remaining 10 ml of dead-space ensures sufficient volume to allow a relatively large amount of saturated vapor to develop for release into the flow control portion 106. In addition, the dead-space reduces the chances of injecting liquid into the flow control portion 106.

In some embodiments, the replaceable cartridge can have an internal volume of about 1 ml to about 1000 ml. In other embodiments, the replaceable cartridge can have an internal volume of about 1 to about 900 ml, about 1 to about 800 ml, about 1 to about 700 ml, about 1 to about 600 ml, about 1 to about 500 ml, about 1 to about 400 ml, about 1 to about 300 ml, about 1 to about 200 ml, about 1 to about 100 ml, about 1 to about 50 ml, or about 1 to about 20 ml. In other embodiments, the replaceable cartridge can have an internal volume of about 1 to about 100 ml, about 100 to about 200 ml, about 300 to about 400 ml, about 400 to about 500 ml, about 500 to about 600 ml, about 700 to about 800 ml, about 800 to about 900 ml, or about 900 to about 1000 ml. In other embodiments, the replaceable cartridge can have an internal volume of about 1 to about 100 ml, about 10 to about 100 ml, about 10 to about 50 ml, about 10 to about 40 ml, about 10 to about 30 ml, or about 10 to about 20 ml.

Figure 7:
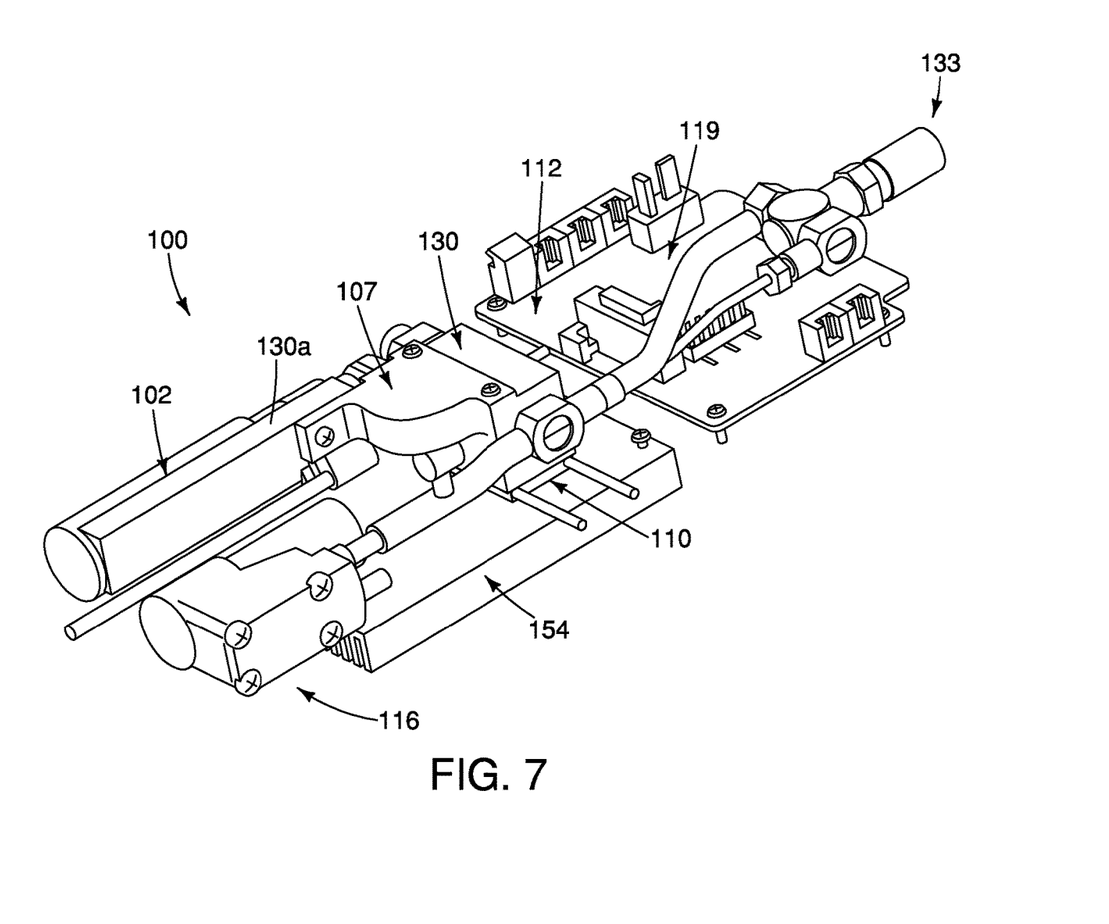
FIG. 7 is a perspective view of an embodiment of an ambulatory device shown without a casing.

As shown in FIG. 2A, the device 100 may also include a manifold 130. The manifold 130 may be a small block of metal, such as stainless steel. The reservoir 102 feeds into the manifold 130 through a quick disconnect fitting 132. From the fitting 132, the manifold 130 feeds the agent from the reservoir 102 into and then back out of the capillary tubing system 107. Finally the manifold 130 interfaces the solenoid valve's inlet and outlet 112 with the now gaseous agent exiting through a small Teflon tube to join with the fresh air at an outlet fitting 133. An outlet connector 135 may extend to the exterior of the casing 120 for attachment of a delivery device for the subject as described below with reference to FIG. 3A. FIG. 7 shows the device 100 assembled together and without the casing.

As discussed above, some embodiments of the device 100 may include the capillary tubing system 107 that receives the gaseous agent from the reservoir 102. The capillary tubing system 107 may be made of fused silica glass with a polymer coating to aid handling and connections. Both the inner diameter (ID) and the length can be varied for large scale changes in agent delivery (i.e. swapping one tube assembly for another). The internal diameter (ID) of the capillary tubing system may be from about 10 microns to about 500 microns. In some embodiments, the ID is between 10 and 20 microns. This diameter severely restricts gas flow to achieve the desired dose range of the agent. For example, when ENO is used as the agent, the dose range is about 0.1-100 ppm. For any given tube, closely-controlling the temperature of the reservoir 102 and the capillary tubing system 107, allows for system pressure and thus flow to be tightly regulated. In some embodiments, the length of the capillary tubing system 107 may also be varied to control the delivery of the agent. The length of the capillary tubing system may be about 1 mm to about 1000 mm. In some embodiments, the capillary tubing system may be provided as a coil. In an example embodiment using ENO liquid as the starting agent, a capillary tube that was 95 mm long with a 20 micron ID delivered about 20 ppm to about 45 ppm ENO as the internal system was heated. In another example embodiment, a capillary tube that was 135 mm long with a 20 micron ID delivered about 3.8-10.5 ppm ENO over a temperature range of 75° F. to 87° F.

In some embodiments, the dose range is about 0.1 ppm to about 100 ppm, 1 ppm to about 100 ppm, about 0.1 ppm to about 50 ppm, or about 50 ppm to about 100 ppm. In other embodiments, the dose range is about 0.1 ppm to about 10 ppm, about 0.1 ppm to about 20 ppm, about 0.1 ppm to about 30 ppm, about 0.1 ppm to about 40 ppm, about 0.1 ppm to about 50 ppm, about 0.1 ppm to about 60 ppm, about 0.1 ppm to about 70 ppm, about 0.1 ppm to about 80 ppm, about 0.1 ppm to about 90 ppm, or about 0.1 ppm to about 100 ppm. In other embodiments, the dose range is about 0.1 ppm to about 20 ppm, about 10 ppm to about 30 ppm, about 20 ppm to about 40 ppm, about 30 ppm to about 50 ppm, about 40 ppm to about 60 ppm, about 50 ppm to about 70 ppm, about 60 ppm to about 80 ppm, about 70 ppm to about 90 ppm, or about 80 ppm to about 100 ppm.

In some embodiments, the dose range is about 0.1 ppm to about 30 ppm, about 1 ppm to about 30 ppm, about 10 ppm to about 40 ppm, about 20 ppm to about 50 ppm, about 30 ppm to about 60 ppm, about 40 ppm to about 70 ppm, about 50 ppm to about 80 ppm, about 60 ppm to about 90 ppm, or about 70 ppm to about 100 ppm.

In some embodiments, the internal diameter (ID) of the capillary tubing system is about 10 microns to about 20 microns, about 20 microns to about 30 microns, about 30 microns to about 40 microns, about 40 microns to about 50 microns, about 50 microns to about 60 microns, about 60 microns to about 70 microns, about 70 microns to about 80 microns, about 80 microns to about 90 microns, about 90 microns to about 100 microns, about 100 microns to about 110 microns, about 110 microns to about 120 microns, about 120 microns to about 130 microns, about 130 microns to about 140 microns, about 140 microns to about 150 microns, about 150 microns to about 160 microns, about 160 microns to about 170 microns, about 170 microns to about 180 microns, about 180 microns to about 190 microns, about 190 microns to about 200 microns, about 200 microns to about 210 microns, about 210 microns to about 220 microns, about 220 microns to about 230 microns, about 230 microns to about 240 microns, about 240 microns to about 250 microns, about 150 microns to about 260 microns, about 260 microns to about 270 microns, about 270 microns to about 280 microns, about 280 microns to about 290 microns, about 290 microns to about 300 microns, about 300 microns to about 310 microns, about 310 microns to about 320 microns, about 320 microns to about 330 microns, about 330 microns to about 340 microns, about 340 microns to about 350 microns, about 350 microns to about 360 microns, about 360 microns to about 370 microns, about 370 microns to about 380 microns, about 380 microns to about 390 microns, about 390 microns to about 400 microns, about 400 microns to about 410 microns, about 410 microns to about 420 microns, about 420 microns to about 430 microns, about 430 microns to about 440 microns, about 440 microns to about 450 microns, about 450 microns to about 460 microns, about 460 microns to about 470 microns, about 470 microns to about 480 microns, about 480 microns to about 490 microns, or about 490 microns to about 500 microns.

In some embodiments, the internal diameter (ID) of the capillary tubing system is about 10 microns to about 50 microns, about 50 microns to about 100 microns, about 100 microns to about 150 microns, about 150 microns to about 200 microns, about 200 microns to about 250 microns, about 250 microns to about 300 microns, about 300 microns to about 350 microns, about 350 microns to about 400 microns, about 400 microns to about 450 microns, or about 450 microns to about 500 microns. In other embodiments, the internal diameter (ID) of the capillary tubing system is about 10 microns to about 100 microns, about 100 microns to about 200 microns, about 200 microns to about 300 microns, about 300 microns to about 400 microns, or about 400 microns to about 500 microns.

In some embodiments, the length of the capillary tubing system is about 1 mm to about 500 mm, about 1 mm to about 400 mm, about 1 mm to about 300 mm, about 1 mm to about 200 mm, or about 1 mm to about 100 mm. In other embodiments, the length of the capillary tubing system is about 1 mm to about 100 mm, about 100 mm to about 200 mm, about 200 mm to about 300 mm, about 300 mm to about 400 mm, or about 400 mm to about 500 mm.

The temperature controller 110 and the thermistor 121 may be used to control the device 100 internal temperature. The temperature controller 110 may be a thermoelectric cooler (TEC) that is a solid-state active heat pump. By passing current through the TEC a temperature difference is realized between the two sides. The TEC is reversible, which allows the device 100 to be heated or cooled depending upon ambient conditions. In addition, the device 100 is arranged such that the capillary tubing system 107 is at a slightly higher temperature than the reservoir 102 (due to the closer proximity of the capillary tube system 107 to the TEC). This gradient creates slightly higher pressures in the downstream side of the capillary tubing system 107, which pushes any condensate back up the capillary tubing system 107 towards the reservoir 102 behind the flowing gas. It also serves as a safety feature: if some liquid agent were to be expelled into the capillary tubing system, the liquid agent would still vaporize by the time the liquid agent flowed out of the capillary tubing system 107.

Figure 3A:
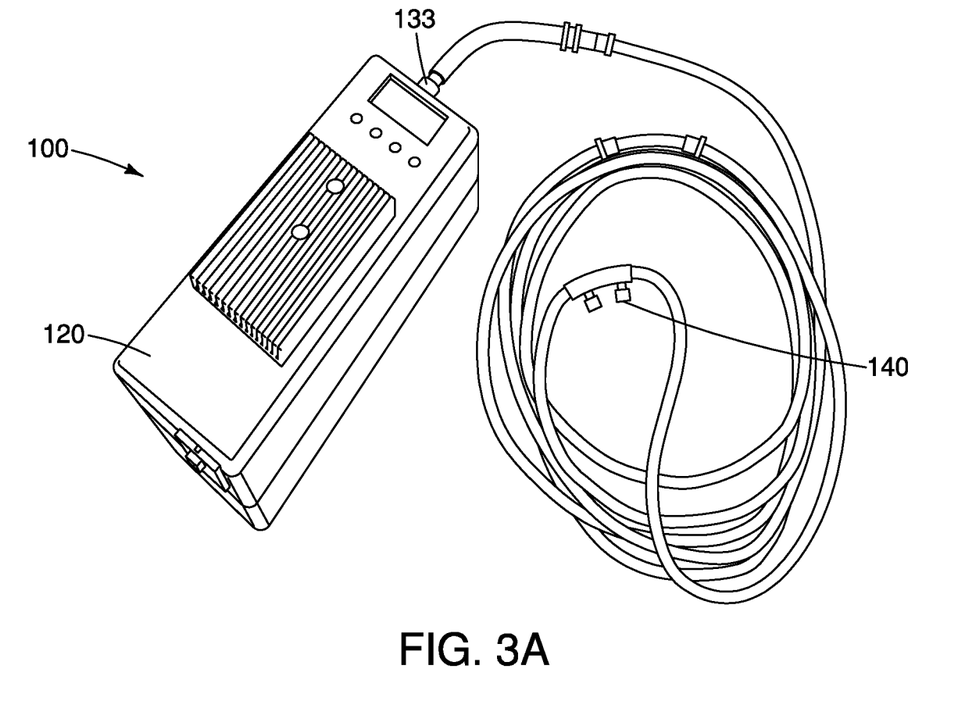
FIG. 3A illustrates an embodiment of an ambulatory device with a delivery device connected to the ambulatory device.

After the exiting the capillary tubing system 107, the agent passes through a solenoid driven control valve 112; this is the secondary means to control agent delivery. The valve 112 is principally used in its ON/OFF operation but can be used in a Pulse Width Modulation for additional flow control including incorporation of an on-demand function (e.g. switched to open upon sensing subject's inspiration). At rest, the valve 112 is closed. This is a second safety feature in that if there is a power failure no agent can be released. The agent in vapor form then flows into a junction where vapor agent is mixed with fresh air supplied by a reciprocating diaphragm of the pump 116. The pump speed can be varied to regulate the concentration and total flow rate of the agent/air mixture out of the device 100. The gas blend then passes into a delivery device 140 to be administered to the subject. As shown in FIG. 3A, the delivery device 140 may be a nasal cannula. Any type of delivery device 140 known in the art for delivering a gas to a subject may be used with the device 100. By way of non-limiting example, when ENO is used, the gas delivered may be about 0.1-100 ppm ENO in air.

The device 100 may include a controller 119 that operates all of the various subsystems. The controller 119 maintains the correct temperature (thermistor feedback), operates the solenoid valve 112 and the air pump 116. The device 100 may also include a power source 138 such as a battery. By way of non-limiting example, the power source 138 may be a two cell (7.4V nominal voltage) Lithium Polymer battery. The battery 138 presently occupies about half of the internal volume of the device 100. Lithium Polymer provides high power density for a secondary (rechargeable) cell. A 5000 mAh battery will run the device 100 for 8+ hours depending on ambient temperatures. The software is a simple menu-based controller that drives the various sub-systems. An ARM Cortex M3 processor, the STM32L151, is used because it is small, low power, and has on-board Digital-to-Analog outputs as well as advanced timers. The source code was compiled with GCC using Rowley's Crossworks for ARM software.

Figure 3B:
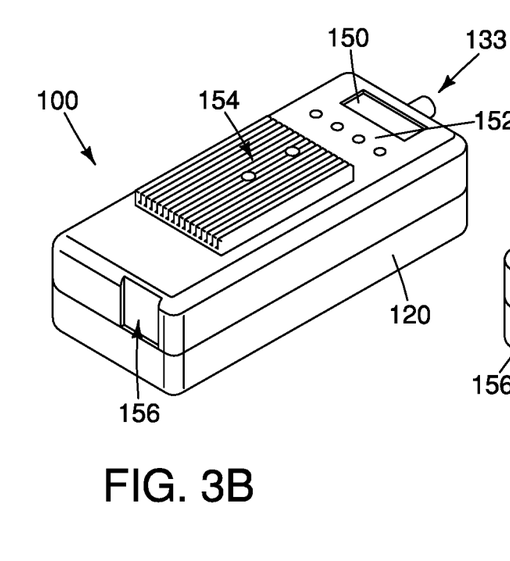
FIG. 3B is a perspective top view of the ambulatory device shown in FIG. 3A.
Figure 3C:
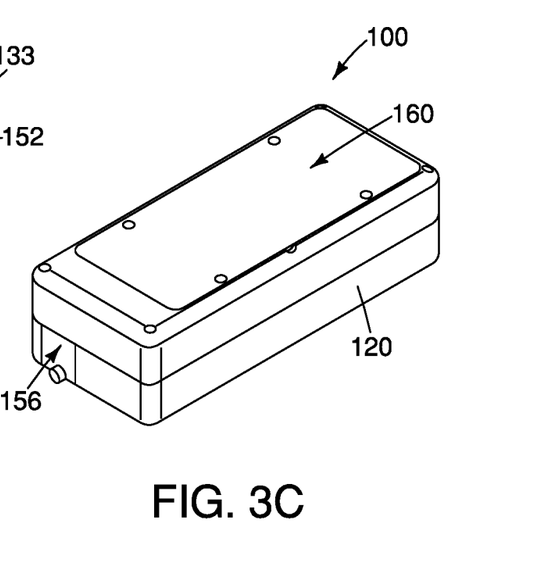
FIG. 3C is a perspective bottom view of the device shown in FIG. 3A.
Figure 6:
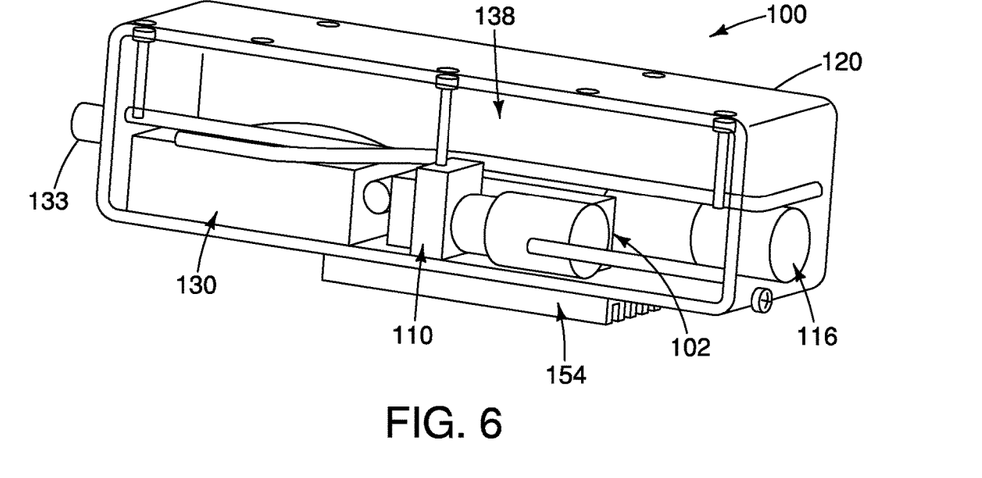
FIG. 6 is a sectional view an embodiment of an ambulatory device.

FIGS. 3B and 3C show exterior views of an embodiment of the device 100. FIG. 3B shows a top view of the device 100 that may include a display 150 and control buttons 152. The display 150 may be used to give the subject feedback from the device 100 and/or to view settings. In some embodiments, the control buttons 152 may be used for programing the device 100, to select different preset programs, to change the display 150, and the like. By way of non-limiting example, the flow rate from the device 100 may be controlled by temperature of the reservoir 102, the valve 112, and the pump 116, and the controller 130 may be used to regulate each of the components to deliver the agent at a specified amount. As shown in FIG. 3B, the device 100 may also include a heat sink 154 to facilitate control of the temperature of the agent for delivery through the device 100. FIGS. 3B and 3C also show a door 156 that provides access to the reservoir 102, for example when a replaceable cartridge is used to supply the agent as described above. FIG. 3C also illustrates a battery cover 160. FIG. 6 illustrates a sectional view of the device 100 with the casing 120 included. In some embodiments, insulation may also be included in the casing 120.

Figure 4:
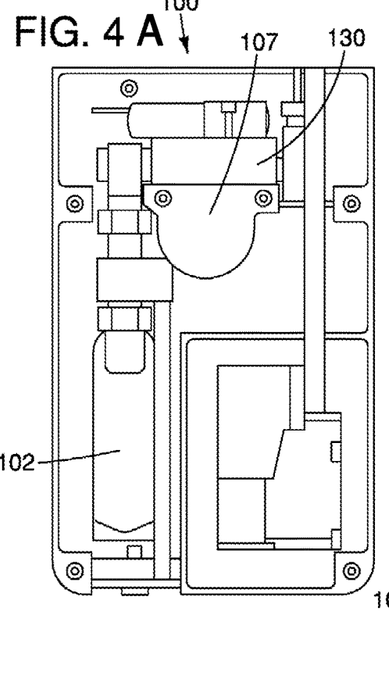
FIG. 4 is a top view comparing two embodiments of an ambulatory device.

FIGS. 4A and B illustrate the device 100 having two different configurations for the manifold 130. In FIG. 4B, the device 100 illustrates a manifold extension 130a that co-extends along a portion of the reservoir 102. In some embodiments, the manifold extension 130a is included to facilitate thermal conduction and even distribution of the temperature control in the reservoir 102 and control flow through the capillary tubing system 107.

In some embodiments, the device 100 may deliver the agent in an amount of about 0.1-100 ppm. In some embodiments, the agent delivered is in an amount of about 0.1 ppm to about 100 ppm, about 0.1 ppm to about 10 ppm, about 0.1 ppm to about 20 ppm, about 0.1 ppm to about 30 ppm, about 0.1 ppm to about 40 ppm, about 0.1 ppm to about 50 ppm, about 0.1 ppm to about 60 ppm, about 0.1 ppm to about 70 ppm, about 0.1 ppm to about 80 ppm, or about 0.1 ppm to about 90 ppm. In other embodiments, the agent delivered is in an amount of about 1 ppm to about 10 ppm, about 1 ppm to about 20 ppm, about 1 ppm to about 30 ppm, about 1 ppm to about 40 ppm, about 1 ppm to about 50 ppm, about 1 ppm to about 60 ppm, about 1 ppm to about 70 ppm, about 1 ppm to about 80 ppm, about 1 ppm to about 90 ppm, or about 1 ppm to about 100 ppm.

In other embodiments, the agent delivered is in an amount of about 0.1 ppm to about 20 ppm, about 5 ppm to about 25 ppm, about 10 ppm to about 30 ppm, about 15 ppm to about 35 ppm, about 20 ppm to about 40 ppm, about 25 ppm to about 45 ppm, about 30 ppm to about 50 ppm, about 35 ppm to about 55 ppm, about 40 ppm to about 60 ppm, about 45 ppm to about 65 ppm, about 50 ppm to about 70 ppm, about 55 ppm to about 75 ppm, about 60 ppm to about 80 ppm, about 65 ppm to about 85 ppm, about 70 ppm to about 90 ppm, about 75 ppm to about 95 ppm, or about 80 ppm to about 100 ppm, In other embodiments, the agent delivered is in an amount of about 0.1 ppm to about 30 ppm, about 1 ppm to about 30 ppm, about 10 ppm to about 40 ppm, about 20 ppm to about 50 ppm, about 30 ppm to about 60 ppm, about 40 ppm to about 70 ppm, about 50 ppm to about 80 ppm, about 60 ppm to about 90 ppm, or about 70 ppm to about 100 ppm. In other embodiments, the agent delivered is in an amount of about 0.1 ppm to about 40 ppm, about 1 ppm to about 40 ppm, about 10 ppm to about 50 ppm, about 20 ppm to about 60 ppm, about 30 ppm to about 70 ppm, about 40 ppm to about 80 ppm, about 50 ppm to about 90 ppm, or about 60 ppm to about 100 ppm.

In some embodiments, the device 100 may be designed to have 2 or more ranges for delivery that may be preset or controlled by the subject. For example, the device 100 may deliver the agent in a first range of about 0.1-10 ppm and a second range of about 1-100 ppm.

The amount of ENO exiting the device 100 may be quantified using Fourier transformed infra-red spectroscopy (FTIR). The device 100 delivered increasing amounts of ENO in response to raising the temperature. The capillary action draws ENO through the capillary tubing system 107 at a fixed, but temperature dependent rate. By controlling the temperature of the ENO in the device 100, the amount of ENO delivered to the subject is controlled.

Figure 8:
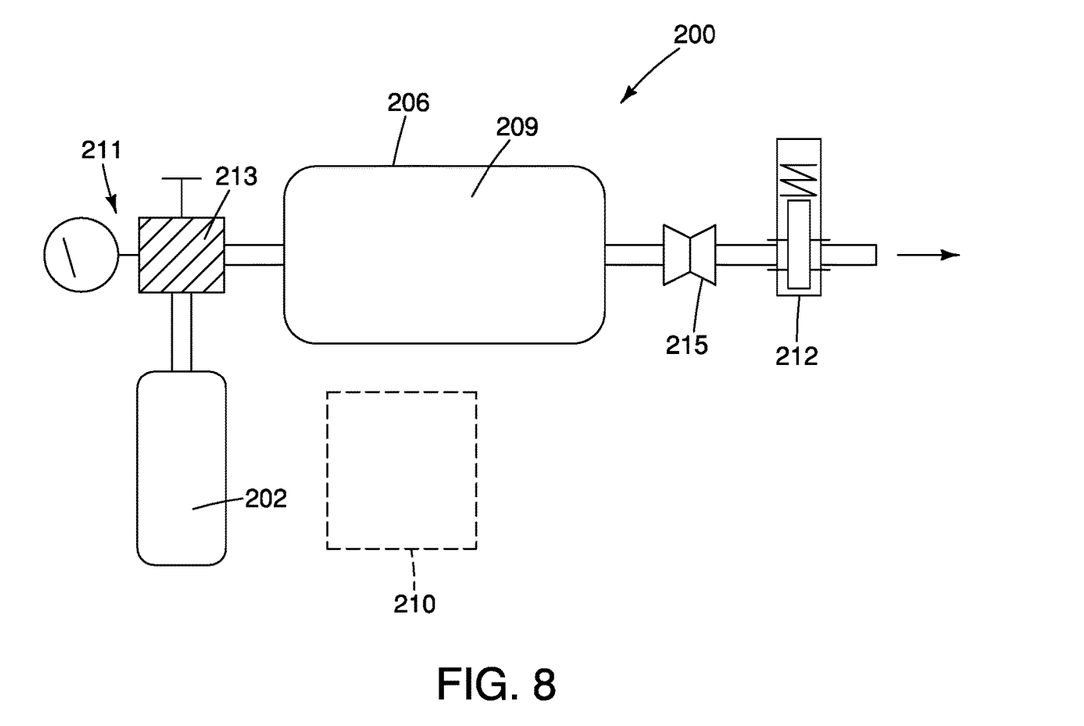
FIG. 8 is a schematic of an embodiment of an ambulatory device.
Figure 9:
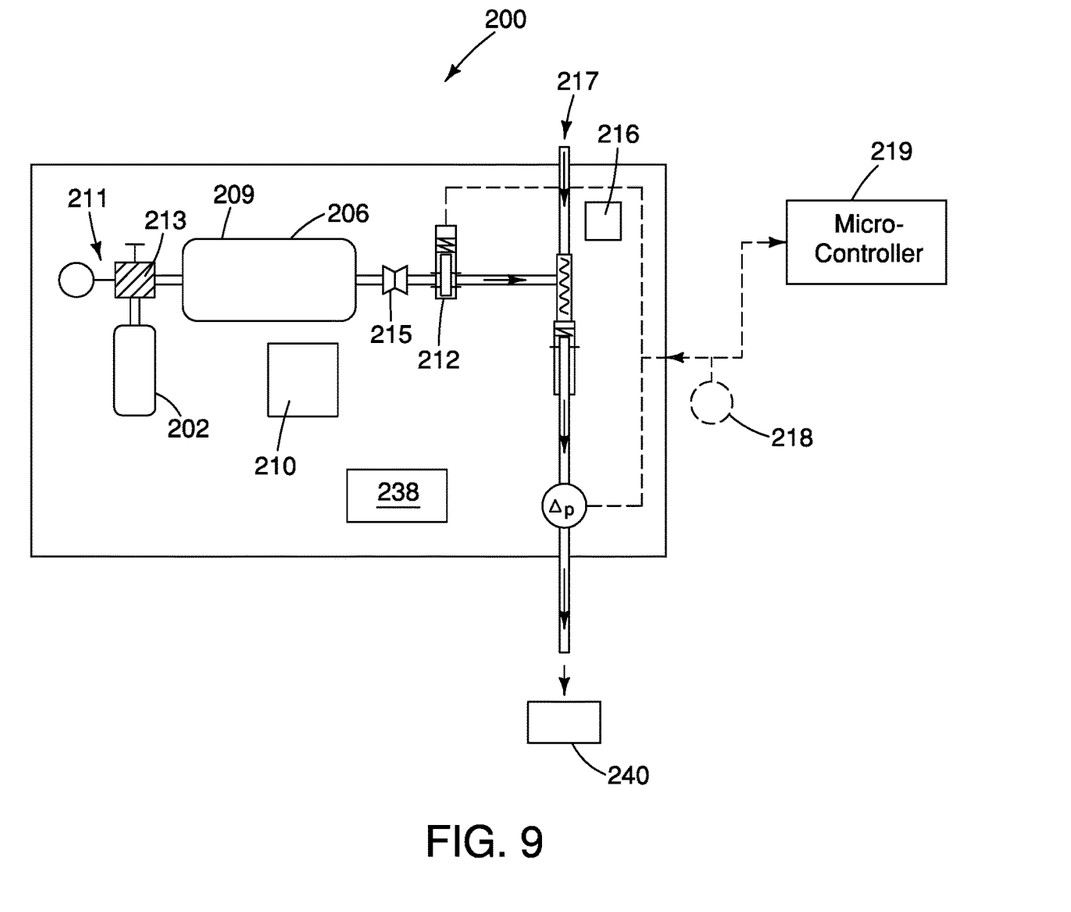
FIG. 9 is a schematic of an embodiment of an ambulatory device.

FIGS. 8 and 9 illustrate schematic views of alternative embodiments of an ambulatory device 200. Similar to the device 100 described above, the device 200 may be used to deliver a nitrosylating agent to a subject. The nitrosylating agent includes but is not limited to the following: ethyl nitrite, amyl nitrite, butyl nitrite, isobutyl nitrite, tert-butyl nitrite and combinations thereof. In some embodiments, the nitrosylating agent is ethyl nitrite (ENO). However, any liquid agent that may be vaporized for delivery to a subject may be delivered using the device 200. The temperature, delivery rate and controller will depend on the agent being delivered.

The device 200 includes a reservoir 202 for storing the agent to be delivered. The agent may be in liquid form in the reservoir 202. The reservoir 202 may be connected to a flow control portion 206 such as a gas expansion chamber 209. The device 200 may include all the features of the device 100 described above with the exception that the flow control portion 206 is a gas expansion chamber instead of a capillary tubing system described above. A temperature controller 210 may be included to control the temperature of the reservoir 202 and/or the gas expansion chamber 209. In some embodiments, no temperature control is included. A pressure gauge 211 may be included to monitor the pressure in the reservoir 202 and a pressure regulator 213 may be used to control the flow of the agent from the reservoir 202 to the gas expansion chamber 209. One or more valves 212 control the flow of agent out of the flow control portion 206 to be delivered to the subject. In some embodiments, a pump 216 may be used to pump the air mixed with the agent. A sensor 218 may be included to monitor or control the amount of the agent that is delivered to the subject. A controller 219 (including, but not limited to, a microcontroller) may be included in the device 200 to monitor and regulate the temperature of the reservoir 202, the temperature controller 210, the valve 212, the pump 216 and the sensor 218.

The device 200 may include a reservoir 202 that stores ENO in a mixed phase (liquid and saturated gas) storage cartridge; storage in liquid form allows for a considerable amount of agent to be included in the device 200 relative to the rate of use. The storage cartridge may be made of steel, such as stainless steel or a polymer, such as polycarbonate. In some embodiments, a stainless steel reservoir 202 may be used to improve the thermal conduction between the temperature controller 210 and the reservoir 202. Similar to the device 100, ENO flow may be controlled by the temperature of the device 200. The device 200 may include a replaceable cartridge, such as a replaceable ENO cartridge 202.

After exiting the flow control portion 206, the agent passes through a solenoid driven control valve 212. A flow restrictor 215 may also be included in the device 200 between the flow control portion 206 and the control valve 212. The valve 212 is principally used in its ON/OFF operation but can be used in a Pulse Width Modulation for additional flow control including incorporation of an on-demand function (e.g. switched to open upon sensing subject's inspiration). At rest, the valve 212 is closed. The agent in vapor form then flows into a junction where vapor agent is mixed with fresh air 217 supplied by the pump 216. The pump speed can be varied to regulate the concentration and total flow rate of the agent/air mixture out of the device 200. The gas blend then passes into a delivery device 240 to be administered to the subject. Any type of delivery device 240 known in the art for delivering a gas to a subject may be used with the device 200. By way of non-limiting example, when ENO is used, the gas delivered may be about 0.1-100 ppm ENO in air. In some embodiments, the gas delivered is about 0.1 ppm to about 100 ppm, about 0.1 ppm to about 10 ppm, about 0.1 ppm to about 20 ppm, about 0.1 ppm to about 30 ppm, about 0.1 ppm to about 40 ppm, about 0.1 ppm to about 50 ppm, about 0.1 ppm to about 60 ppm, about 0.1 ppm to about 70 ppm, about 0.1 ppm to about 80 ppm, or about 0.1 ppm to about 90 ppm. In other embodiments, the gas delivered is about 1 ppm to about 10 ppm, about 1 ppm to about 20 ppm, about 1 ppm to about 30 ppm, about 1 ppm to about 40 ppm, about 1 ppm to about 50 ppm, about 1 ppm to about 60 ppm, about 1 ppm to about 70 ppm, about 1 ppm to about 80 ppm, about 1 ppm to about 90 ppm, or about 1 ppm to about 100 ppm.

In other embodiments, the gas delivered is about 0.1 ppm to about 20 ppm, about 5 ppm to about 25 ppm, about 10 ppm to about 30 ppm, about 15 ppm to about 35 ppm, about 20 ppm to about 40 ppm, about 25 ppm to about 45 ppm, about 30 ppm to about 50 ppm, about 35 ppm to about 55 ppm, about 40 ppm to about 60 ppm, about 45 ppm to about 65 ppm, about 50 ppm to about 70 ppm, about 55 ppm to about 75 ppm, about 60 ppm to about 80 ppm, about 65 ppm to about 85 ppm, about 70 ppm to about 90 ppm, about 75 ppm to about 95 ppm, or about 80 ppm to about 100 ppm, In other embodiments, the gas delivered is about 0.1 ppm to about 30 ppm, about 1 ppm to about 30 ppm, about 10 ppm to about 40 ppm, about 20 ppm to about 50 ppm, about 30 ppm to about 60 ppm, about 40 ppm to about 70 ppm, about 50 ppm to about 80 ppm, about 60 ppm to about 90 ppm, or about 70 ppm to about 100 ppm. In other embodiments, the gas delivered is about 0.1 ppm to about 40 ppm, about 1 ppm to about 40 ppm, about 10 ppm to about 50 ppm, about 20 ppm to about 60 ppm, about 30 ppm to about 70 ppm, about 40 ppm to about 80 ppm, about 50 ppm to about 90 ppm, or about 60 ppm to about 100 ppm.

The device 200 may include a controller 219 that operates all of the various subsystems. The controller 219 maintains the correct temperature (thermistor feedback) and operates the solenoid valve 212 and the air pump 216. The device 200 may also include a power source 238 such as a battery similar to the battery described above.

Table I shows an example of general device characteristics.

TABLE I

| | General Device Characteristics | | | |
|---|---|---|---|---|
| Specification | Description | Metric | Units | Details/Notes |
| Physical | | | | |
| Size | Physical volume of device | 175 | cm³ | approximately 3.5" × 3" × 1" or similar volume |
| Weight | Total weight of system | 250 | g | Goal will be to under this value |
| Carrying System | How the User will carry or wear device | | | Belt and MOLLE compatible attachment system |
| Electrical | | | | |
| Battery Type | Rechargeable battery pack | | | Lithium Polymer battery is first choice |
| Battery Life | Operation time without battery change or charge | 24 | hr | minimum, longer battery life will depend on final size and weight |
| Environmental | | | | |
| Water Proofing | Units ability to tolerate water | IPX 4 | N/A | IP Code based; Protected against splashing water - Same as IPX-3 but water is sprayed at all angles. IPX 7 would be water proof to 1 m and might be desired |

TABLE I-continued

General Device Characteristics

| Specification | Description | Metric | Units | Details/Notes |
|---|---|---|---|---|
| High Temp | Maximum Operation Temp | 85 | C | |
| Low Temp | Minimum Operation Temp | −30 | C | |
| Shock Tolerance | Drop distance system must survive | 1.5 | m | Drop free onto a hard surface |
| Altitude | Altitude at which the unit will function | sea level - 25000 | ft | |
| User Interface | | | | |
| Power Switch | Switch that powers the unit on and off | | | |
| Input Buttons | For selection of modes and system info | | | |
| Interface Screen | Alpha Numeric display for giving user feedback | | | |
| Nasal Cannula | For delivery of ENO/Air to user | | | |
| Notification system | Way to get the users attention | | | like small vibrator to notify user of system message (low battery, not breathing through nose, etc) |
| Drug Delivery | | | | |
| Range | dosage level the system can deliver | 0.1-100 | ppm | System will be designed for 2 or more ranges spanning 0.1-100 ppm, likely will be a 0.1-10 ppm and a 1-100 ppm ranges. |
| Accuracy | How close actual dosage is to input value | 3 | % | This is presently a conservative estimate and need more research |
| Supply Size | Operation time between ENO recharges | 3 | day | |
| On demand | only release ENO on inspiration | | | |

It is therefore intended that the foregoing detailed description be regarded as illustrative rather than limiting, and that it be understood that it is the following claims, including all equivalents, that are intended to define the spirit and scope of this invention.

The invention claimed is:

1. A device for delivering a controlled concentration of an agent, the device comprising:
a reservoir for the agent, wherein the agent is stored in a vapor phase or a liquid phase that transforms to a vapor phase depending on a temperature of the agent;
a flow control portion operably connected to the reservoir for flowing the vapor phase of the agent out of the reservoir, wherein the vapor phase of the agent is propelled by a vapor pressure;
a temperature control unit for controlling the vapor pressure based on a temperature inside the reservoir and/or the flow control portion;
a valve for releasing the vapor phase of the agent from the flow control portion; and
a pump for flowing air to mix with the vapor phase of the agent released by the valve and for flowing the mixture of the vapor phase of the agent and air out of the device to a subject.

2. The device according to claim 1, wherein the flow control portion comprises a capillary tubing system.

3. The device according to claim 2, wherein the length of the capillary tubing system is about 1 mm to about 1000 mm.

4. The device according to claim 1, wherein the flow control portion comprises a gas expansion chamber.

5. The device according to claim 1, the flow control portion further comprising a manifold operably connected to the reservoir.

6. The device according to claim 1, further comprising a controller for controlling the flow of the vapor phase of the agent through the device.

7. The device according to claim 6, wherein the controller controls the pump and/or the temperature of the reservoir and/or the flow control portion.

8. The device according to claim 1, wherein the reservoir comprises a replaceable cartridge.

9. The device according to claim 1, wherein the reservoir comprises stainless steel.

10. The device according to claim 1, further comprising a battery.

11. The device according to claim 1, wherein the liquid phase of the agent comprises liquid ethyl nitrite.

12. A device for delivering a controlled concentration of an agent, the device comprising:
a reservoir for the agent;
a flow control portion operably connected to the reservoir and comprising a portion of a manifold that co-extends along at least a portion of the reservoir;
a valve for releasing the agent from the flow control portion; and
a pump for flowing air to mix with the agent released by the valve and for flowing the mixture of the agent and air out of the device to a subject.

13. A method of delivering a vaporized agent to a subject, the method comprising:
    storing a liquid agent in a reservoir of a device, wherein the device further comprises a flow control portion in communication with the reservoir and stoppered by a valve;
    controlling a temperature of the device to vaporize a portion of the liquid agent into a vaporized agent in gas form in the reservoir;
    mixing the vaporized agent with air in the device; and
    flowing the mixture of vaporized agent and air out of the device to the subject.

14. The method according to claim 13, further comprising heating the liquid agent.

15. The method according to claim 13, comprising delivering the agent to the subject at a range of about 0.1-100 ppm.

16. The method according to claim 13, wherein the liquid agent comprises liquid ethyl nitrite.

17. The method according to claim 13, further comprising controlling an amount of the vaporized agent delivered to the subject by controlling the temperature in the device.

18. The method according to claim 13, further comprising controlling a rate of flow out of the flow control portion with the valve.

19. The method according to claim 13, wherein the device for delivering the agent to the subject is an ambulatory device.

* * * * *

UNITED STATES PATENT AND TRADEMARK OFFICE
CERTIFICATE OF CORRECTION

PATENT NO. : 11,577,042 B2
APPLICATION NO. : 16/619202
DATED : February 14, 2023
INVENTOR(S) : Jonathan S. Stamler Page 1 of 1

It is certified that error appears in the above-identified patent and that said Letters Patent is hereby corrected as shown below:

In the Specification

Column 1, Lines 13-19. Delete "FEDERALLY SPONSORED RESEARCH OR DEVELOPMENT This invention was made with government support under federal grant number N66001-10-2015 awarded by Defense Advanced Research Projects Agency. The government has certain rights in the invention."

Insert -- GOVERNMENT FUNDING
This invention was made with government support under NS025713 awarded by the National Institutes of Health. The government has certain rights in the invention. --

Signed and Sealed this
Third Day of June, 2025

Coke Morgan Stewart
*Acting Director of the United States Patent and Trademark Office*